(12) United States Patent
Della Valle et al.

(10) Patent No.: US 8,470,373 B2
(45) Date of Patent: *Jun. 25, 2013

(54) COMPOSITION CONTAINING ULTRA-MICRONIZED PALMITOYL-ETHANOLAMIDE

(75) Inventors: Francesco Della Valle, Padova (IT); Gabriele Marcolongo, Due Carrare (IT); Maria Federica Della Valle, Padova (IT)

(73) Assignee: Epitech Group S.r.l., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/120,408

(22) PCT Filed: Sep. 7, 2009

(86) PCT No.: PCT/IT2009/000399
§ 371 (c)(1),
(2), (4) Date: Mar. 22, 2011

(87) PCT Pub. No.: WO2011/027373
PCT Pub. Date: Mar. 10, 2011

(65) Prior Publication Data
US 2011/0171313 A1 Jul. 14, 2011

(51) Int. Cl.
*A61K 9/1694* (2006.01)
(52) U.S. Cl.
USPC ......................................................... 424/489

(58) Field of Classification Search
None
See application file for complete search history.

(56) References Cited

U.S. PATENT DOCUMENTS 6,548,550 B1 * 4/2003 Comelli et al. ............... 514/625

FOREIGN PATENT DOCUMENTS

| CA | 2582027 A1 * | 9/2007 |
|---|---|---|
| EP | 0 550 006 A2 | 7/1993 |
| EP | 1 844 787 A1 | 10/2007 |
| WO | WO 96/18391 A2 | 6/1996 |
| WO | WO 01/10434 A1 | 2/2001 |
| WO | WO 2008/075979 A2 | 6/2008 |

* cited by examiner

*Primary Examiner* — Michael G Hartley
*Assistant Examiner* — Robert Cabral
(74) *Attorney, Agent, or Firm* — Dickstein Shapiro LLP

(57) ABSTRACT

The present invention relates to a composition for pharmaceutical or veterinary use, comprising palmitoylethanolamide. In particular, the present invention relates to a pharmaceutical composition for human or veterinary use, containing a therapeutically efficient amount of palmitoylethanolamide in the ultra-micronized form, wherein more than 90% by weight of palmitoylethanolamide has particle sizes lower than 6 microns, together with pharmaceutically acceptable excipients.

10 Claims, 5 Drawing Sheets

MDSC of original PEA

XRD of orignal PEA

XRD of ultra-micronized PEA

COMPOSITION CONTAINING ULTRA-MICRONIZED PALMITOYL-ETHANOLAMIDE

FIELD OF THE INVENTION

The present invention relates to a composition for pharmaceutical or veterinary use, comprising palmitoylethanolamide.

DESCRIPTION OF THE STATE OF THE ART

In recent years, the concept of "neuroimmunogenic inflammation" has been widely developed, and important progresses have been made in understanding the biological mechanisms behind this widespread type of tissue inflammation, which is primarily induced by the release of given substances by the terminals of primary sensory neurons. Furthermore, it has been shown that small-diameter sensitive fibres participate in the neuroimmunogenic inflammation phenomenon, which fibres are responsive to capsaicin—the plant vanilloid that is present in the red chili pepper—, and that given neuropeptides, which are released by the above-mentioned nerve fibres—particularly, the Substance P (SP) and the Calcitonin Gene-Related Peptide (CGRP)—represent the main peptides responsible for the occurrence of neuroimmunogenic inflammation peripherally.

The possibility to regulate the excitability of the sensory—both nociceptive and pruriceptive—neurons currently has a relevant and increasing therapeutic importance in a wide number of diseases affecting the tissues of peripheral organs, both in man and animals.

Then, the most recent researches have put into focus the role that a specific family of receptors, called TRPV, and in particular the receptor TRPV1—initially known as capsaicin receptor VR1—plays in the process of neurogenic inflammation, and in particular in the hyperalgic phenomena associated thereto.

From the clinical point of view, the outcomes of the new knowledge on the neuroimmunogenic inflammation mechanisms result to be of great interest in the Irritable Bowel Syndrome, in the interstitial cistitis, in the vulvodynias and vestibulodynias, in the vulvar vestibulitis, and in the chronic abacterial prostatitis, in the endometrial lesions, in the miastenia gravis, in the arthropathies of traumatic or degenerative or immunologic origin, affecting the joints, in the painful diseases of the intervertebral discs due to neoinnervation and neovascolarization of the cartilaginous tissue and the annexed ligamentous structures, in the cephalalgic syndromes due to inflammation of the meningeal tissue, in the inflammatory states of the mucous and mucocutaneous tissues of the oral cavity and the dental pulp, in the recurrent fevers with auto-inflammatory basis of PFAPA type, particularly, even if not exclusively, in the pediatric age, in the postherpetic neuralgia, in the adherential syndromes due to peritonitis and/or laparotomic and/or laparoscopic surgical events. The perspectives given by the biomedical research in recent years are of great interest, in relation to neuroimmunogenic inflammation, both acute and chronic, at the skin level, as well as to implications between neuroimmunogenic cutaneous inflammation to psychogenic stimuli, such as stress, that configure more and more clearly a tight connection between brain and skin. This is of great importance in planning innovative pharmacologic approaches in a series of dermatites of a erythematous-squamous nature, in the human and veterinary field (atopic dermatitis, irritative contact dermatitis, allergic contact dermatitis) characterized by itch, burning, local irritation, cutaneous rash, etc., as well as in chronic inflammatory diseases of the granulomatous type at the level of the dermo-epidermal, and more generally, the connective tissues.

The neuroinflammation at the level of the spinal cord nervous structures is characterized by the activation and proliferation of the microglial cells, which are normally present at the spinal level in a quiescent state; such activation, mainly induced by the chronic and/or neuropathic pain, concurs in a relevant manner to the amplification of the pain stimuli deriving chronically from the Peripheral Nervous System, or due to damages localized in the brain, as well as to the development of neurodegeneration through the microglial release of inflammatory mediators, and particularly of the pro-inflammatory cytokine TNF-alpha, interleukin IL-1 beta, and NGF. The activation and proliferation process of the microglia at the level of the spinal cord further plays an extraordinarily important role in the determination of neuropathic pain consequent to damages to the same nervous structures of the spinal cord: in fact, the activated microglia maintains an intense cytokine communication with the spinal cord neurons. All of this is very important in diseases that originate from distresses, primarily of the spinal cord, such as the medullary canal stenoses and the traumatic lesions from flexo-extension of the spine (whiplash injury), and in diseases that, although depending on encephalic neuronal damages, due to the activation effect of cells that are present in the spinal cord (in particular the microglia), induce the symptomatology characteristic of hyperalgic pain (Central Pain Syndrome) and, in given situations, of spasticity; in particular, these are phenomena that are related to diseases such as Amyotrophic Lateral Sclerosis (ALS), Multiple Sclerosis, post-stroke situations, Parkinson's disease, and fibromyalgic syndrome.

The neuroinflammation at the level of the brain neronal structures, today better defined as reactive glyosis, currently represents one of the most interesting topics for the Neurosciences: in particular, the cause-and-effect relationship between the presence of neuroinflammatory processes and neuronal degenerative damage (neurodegenerazione) is more and more clearly defined, with the observation that the neuroinflammation due to the activation and proliferation of non-neuronal cells, such as microglia and astrocytes that are present in the brain, represents the true cause for the degenerative damage affecting the neuron. Moreover, it is evident how the activation of microglia and astrocytes is induced and amplified by pro-inflammatory signals, also of autocrine provenience, such as the TNFα and IL1β. The neuroinflammation has been recognized as being an important causal factor in many degenerative and traumatic diseases affecting the CNS, such as Parkinson's disease, Alzheimer's disease, stroke, cranial trauma.

A highly innovative approach in order to intervene pharmacologically on diseases supported by tissue neuroimmunogenic inflammation, or spinal neuroinflammation, or neuroinflammation of the encephalic nervous structures may consist in the modulation, by means of various mechanisms, of the activation of the non-neuronal cells controlling the peripheral and central sensitization of the neuronal cells, without thereby having to necessarily act directly on the neuron.

Furthermore, it has to be considered, in particular, that a number of non-neuronal cells, belonging to the immune system such as, for example, the microglia, are capable of expressing the cannabinoid CB2 receptor when suitably activated. The endocannabinoid 2-arachidonoylglycerol (2-AG) has been recognized in recent years as the true endogen cannabinoid CB2 receptor ligand, and therefore, as an endogen substance that is capable of modulating the activating and proliferative response of immune progenitor cells strictly related to the sensitization processes of the peripheral and spinal neurons.

Therefore, the object of the present invention is to provide a pharmaceutical composition for the treatment of diseases related to neurogenic inflammation or neuroinflammation, both at the level of peripheral organs and centrally.

Such object is achieved by a composition containing palmitoylethanolamide as defined in the annexed claims, the definitions of which form an integral part of the present description.

DESCRIPTION OF THE INVENTION

Figure 1:
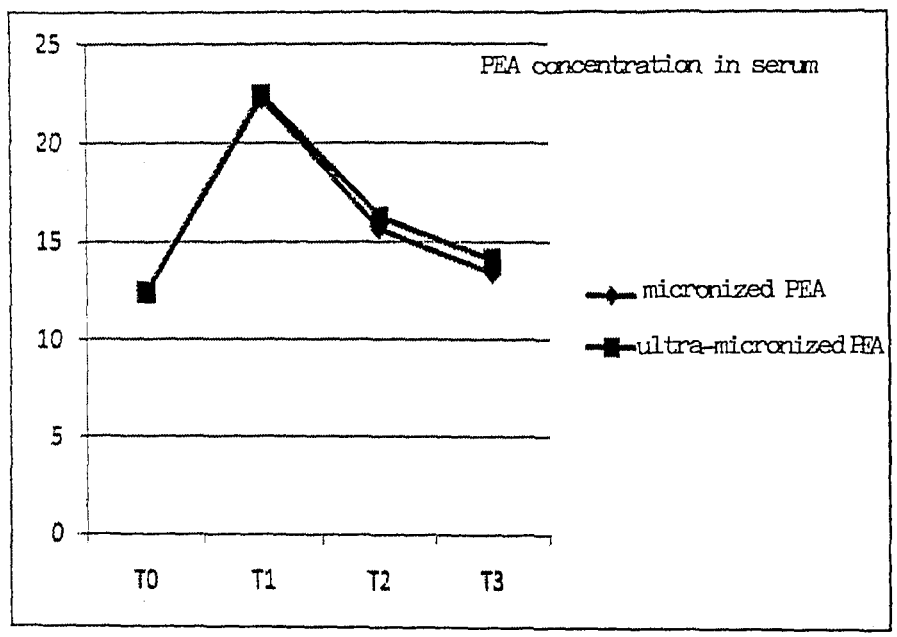
FIG. 1 shows a graph illustrating the concentration of PEA in serum in animals treated with PEA or ultra-micronized PEA according to the invention, as a function of time.
Figure 2:
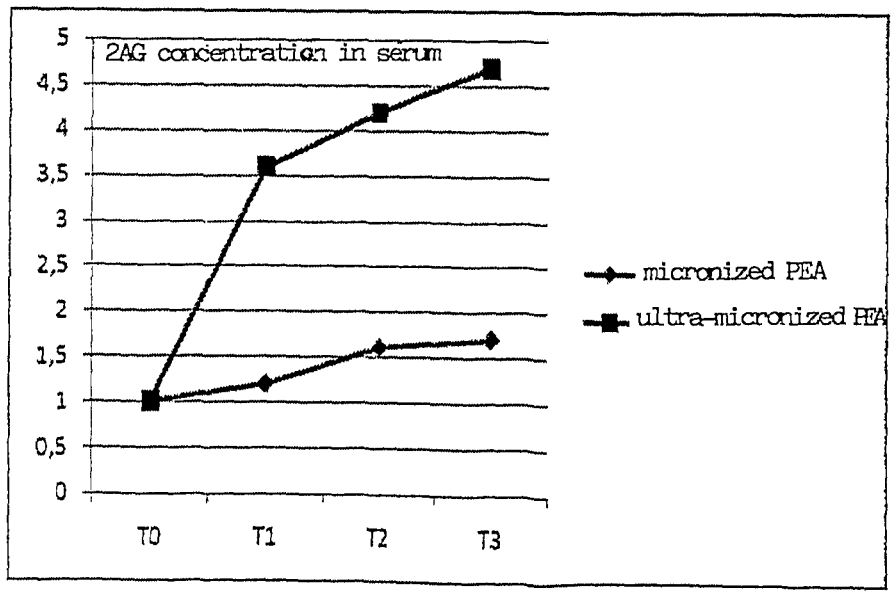
FIG. 2 shows a graph illustrating the concentration of 2-AG (2-arachidonoylglycerol) in serum in animals treated with PEA or with ultra-micronized PEA according to the invention, as a function of time.

The pharmaceutical composition of the invention contains palmitoylethanolamide (PEA) in the ultra-micronized form, wherein more than 90% by weight of palmitoylethanolamide has particle sizes lower than 6 microns.

It has been surprisingly noticed that such a composition, compared to known compositions containing PEA in micronized form, is provided with a high ability to peripherally and centrally act towards inflammatory diseases of the neurogenic or neuroinflammatory type.

Palmitoylethanolamide, a substance of lipidic nature, is hardly subjected to micronization methods, due to the easiness with which it tends to form aggregates; furthermore, the micronization in mechanical energy mills tends to heat the particles to be crushed, and therefore it promotes such aggregation phenomenon, in practice being in contrast with the desired object to decrease the compound particle size to a micrometer level.

Previously, a micronization of the palmitoylethanolamide had been obtained, as described in EP 1 207 870 B1. Although the micronized PEA had, in the treatment of some specific diseases, improved characteristics compared to the non-micronized one, there were no expectation that an effect could be obtained also in neuroinflammatory diseases of the type that is treated in the present invention, nor there was a motivation to push the micronization beyond the threshold of the particle size obtained, both because there were no particular justifications, and because, considered the lipidic nature of the substance subjected to the micronization process, the hope for a success with the conventional technologies was incredibly low. In the tests that were initially carried out, in fact, a trend of the product to generate waxy agglomerates had been noticed, also due to the temperature rise for prolonged dwelling times of the product particles in the micronization chamber, which are necessary to obtain a more efficient micronization.

Therefore, in spite of the existing prejudices in the field, the present inventors have surprisingly found that, by operating with a fluid jet micronization process (that will be hereinafter referred to as "ultra-micronization"), and by suitably modifying the parameters of such process, it is possible to obtain a still more efficient micronization, i.e., a particle distribution of PEA with particle sizes that are statistically lower than those obtainable with the conventional micronization methods.

The product obtained following ultra-micronization has been further characterized in comparison to the original product by a) MDSC (Modulated Differential Scanning calorimetry), and b) XRD (X-Ray Diffraction) with the aim to detect possible structural modifications induced by the ultra-micronization process. Surprisingly, the inventors have found that the ultra-micronized product shows a MDSC and XRD profile that is completely different from the original product, thus demonstrating the appearance, after ultra-micronization, of a different crystalline structure with a higher energy content.

Still more surprisingly, the inventors have found that such new particle size profile of the PEA, and such different crystalline structure characterized by a higher energy content, corresponds to an exponentially increased pharmacological activity compared to the micronized PEA described in EP 1 207 870 B1, in diseases related to neurogenic inflammation or neuroinflammation, therefore both peripherally and centrally.

The ultra-micronization process of the present invention is carried out in a fluid jet plant (for example, the plant model Jetmill®) operating with a pressurized air jet "spiral technology" that is capable of exploiting the kinetic energy—in place of the mechanical energy—to crush the palmitoylethanolamide particles. Such pieces of equipment are conventional, therefore they will not be further described.

In the described plant there are no mobile parts, and the product remains within the crushing disc for a very short time; the fluid threads that are generated within the micronization chamber allow accelerating the particles so that they can reach particularly high speeds, such as to generate a sufficient energy so that they are crushed through a very high number collisions with each other and, as the current inventors found in the case the ultra-micronization process, to induce the modifications of the crystalline structure with the appearance of crystals characterized by a higher energy content; the higher is the speed of the particles, the higher the generated energy will be.

In the ultra-micronization process, such technology has been further modified, and it provides for:
an increase of the micronization chamber inner diameter from 200 to 300 mm;
an increase of the fluid jet (air) pressure from 7÷8 Bars to 10÷12 Bars;
a reduction of the product feeding from 20÷25 Kg/h to 9÷12 Kg/h.

In an embodiment, the palmitoylethanolamide is crystallized in the presence of a vinyl polymer before the ultra-micronization step. In such embodiment, the preferred vinyl polymer is polyvinylpyrrolidone. The crystallization can occur from various solvents, but the solvent of choice is ethanol. In a preferred aspect, the ratio of PEA and polyvinylpyrrolidone is about 30:1.

The following table I shows the particle size profile of ultra-micronized PEA compared to the particle size profile obtained with the micronization according to EP 1 207 870 B1.

TABLE I

| Particle size | Product A Micronized palmitoylethanolamide | Product B Ultra-micronized palmitoylethanolamide |
| --- | --- | --- |
| >14 microns | Traces | Absent |
| <10 microns | About 96% | 100% |
| <6 microns | 80% | 99.9% |
| <2 microns | Not indicated | 59.6% |
| <1 microns | Not indicated | 14.7% |
| <0.6 microns | Non indicated | 2.0% |

In order to measure the particle size, a laser particle size analyzer (Malvern Mastersizer) with LALLS (Low Angle Laser Light Scattering) technique using the Fraunhofer theory of computation is employed.

Modulated Differential Scanning calorimetry (MDSC) and XRD (X-Ray Diffraction) tests have been carried out on the thus-obtained product.

The MDSC technique is a known one, the principles and applications of which are described, for example, in S. R. Rabel et al., Journal of Pharmaceutical and Biomedical Analysis, 21 (1999) 339-345. The tests described in the present patent application have been carried out with an equipment TA DSC Q200.

Figure 3:
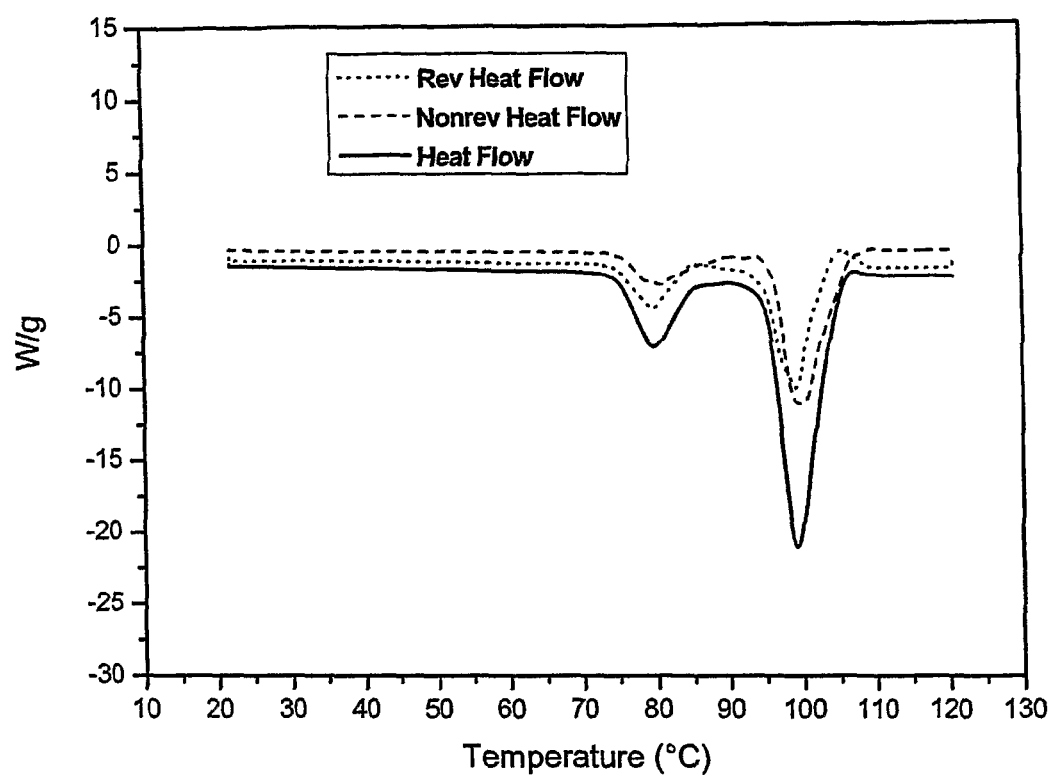
FIG. 3 shows a graph of MDSC (Modulated Differential Scanning calorimetry) of original. PEA.
Figure 4:
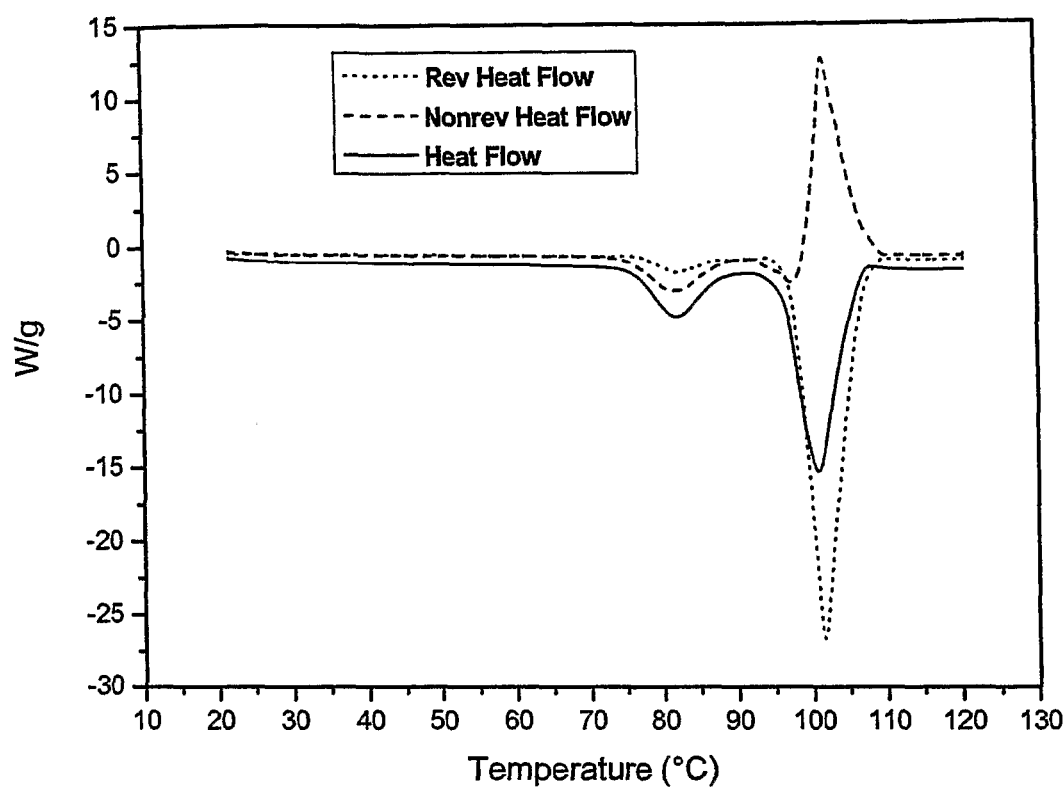
FIG. 4 shows a graph of MDSC (Modulated Differential Scanning calorimetry) of ultra-micronized PEA according to the invention.

Such differential calorimetry measurement performed with the MDSC technique have shown an outstanding difference between the initial product and the ultra-micronized product, which difference consists in the appearance, in the product subjected to ultra-micronization, of a positive peak of exothermal transition at a temperature between 101° C. and 103° C., which is distinctive of structures with a high energy content; in the original product, such peak results, on the contrary, to be negative (see FIGS. 3 and 4). The positive exothermal transition peak has to be interpreted as the signal of the heat developed by the transformation of the higher energy content form (formed during the ultra-micronization process) into the native crystalline form with lower energy content.

The MDSC spectrum analysis of ultra-micronized PEA seems to suggest that the high energy crystalline form obtained via the ultra-micronization process of the present invention is substantially stable at room temperature, since it is converted back into the original low energy form only at temperatures that are near to the product melting point. The net energy transition which characterizes the positive peak at 101-103° C. of FIG. 4 is symptomatic of such stability. Differently, progressive transitions at lower temperatures should have to be noticed.

Figure 5:
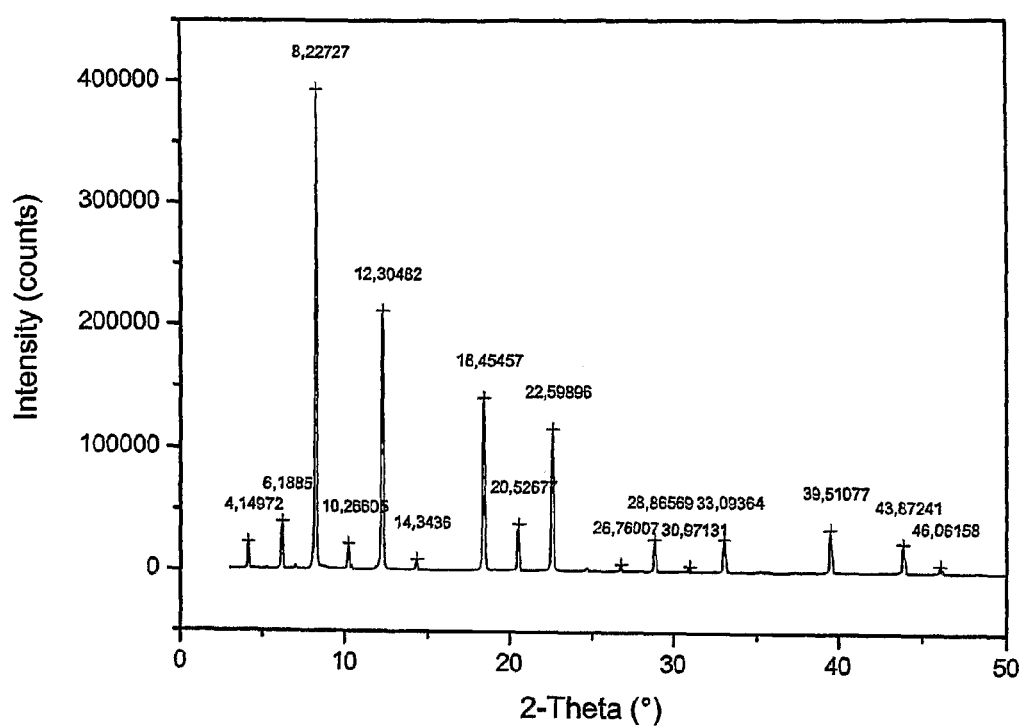
FIG. 5 shows a graph of XRD (X-Ray Diffraction) of original PEA.
Figure 6:
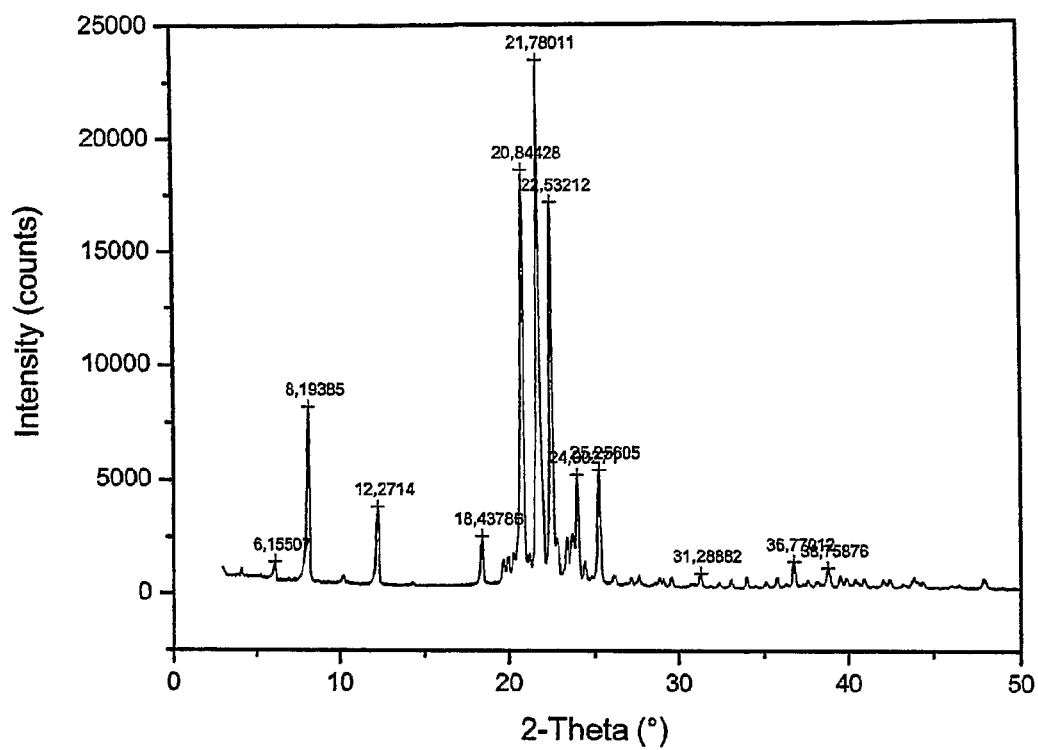
FIG. 6 shows a graph of XRD (X-Ray Diffraction) of ultra-micronized PEA according to the invention.

The X-ray diffraction measurements performed with the XRD technique (an XPERT-PRO equipment has been used) with the aim of investigating solid state of the products, show a particularly significant difference between the diffraction spectra that have been obtained; the spectrum of the product subjected to ultra-micronization confirms the presence of a different crystalline structure compared to the original product (see FIGS. 5 and 6).

The positions and intensity of the individual peaks in the two products are reported herein below.

| XRD Peaks of original PEA | |
| --- | --- |
| Peak [2-Theta(°)] | Relative intensity (counts) |
| 4.150 | 23205 |
| 6.189 | 40155 |
| 8.227 | 393015 |
| 10.266 | 21864 |
| 12.305 | 211389 |
| 14.344 | 9087 |
| 18.455 | 141011 |
| 20.527 | 38771 |
| 22.599 | 115799 |
| 26.760 | 6111 |
| 28.866 | 26906 |
| 30.971 | 4861 |
| 33.094 | 27098 |
| 39.511 | 35388 |
| 43.872 | 24259 |
| 46.062 | 6122 |

| XRD Peaks of PEA ultramicronized | |
| --- | --- |
| Peak [2-Theta(°)] | Relative intensity (counts) |
| 6.155 | 1396 |
| 8.194 | 8191 |
| 12.271 | 3809 |
| 18.438 | 2524 |
| 20.844 | 18585 |
| 21.780 | 23452 |
| 22.532 | 17160 |
| 24.003 | 5214 |
| 25.256 | 5429 |
| 31.289 | 915 |
| 36.770 | 1422 |
| 38.759 | 1138 |

Biological Section

Biochemical Tests

Dose measurements in blood have been carried out of 2-arachidonoyl-glycerol (2-AG), an endocannabinoid of great importance in the modulation of the activation of cells capable of expressing the cannabinoid CB2receptor; this is the case of many cells belonging to the immune system as the microglia.

The tests have been carried out in Beagle dogs by administering, under fasting conditions, an aqueous suspension of palmitoylethanolamide in 0.5% carboxymethyl cellulose; the animal was administered, in single administration, 15 mg/Kg of micronized palmitoylethanolamide and ultra-micronized palmitoylethanolamide, respectively. Blood samples at time 0 (immediately before the administration of palmitoylethanolamide) and at times 1 h, 2 h, 3 h have been taken; the blood was centrifuged and immediately frozen at −80° C.

The dose measurements of palmitoylethanolamide (PEA) and 2-arachidonoylglycerol (2-AG) have been performed with mass spectrometry method as described in Darmani et al., Neuropharmacology (2005); 48: 1154-1163.

The data are reported in table II.

TABLE II

| Administered treatment | Concentration in serum in pmol/mL | | | | | | | |
|---|---|---|---|---|---|---|---|---|
| | Time 0 | | Time 1 h | | Time 2 h | | Time 3 h | |
| | PEA | 2AG | PEA | 2AG | PEA | 2AG | PEA | 2AG |
| Micronized palmitoylethanolamide (Group A - 6 animals) | 12.4 | 1.0 | 22.2 | 1.2 | 15.6 | 1.6 | 13.4 | 1.7 |
| Ultra-micronized palmitoylethanolamide (Group B - 6 animals) | 12.4 | 1.0 | 22.4 | 3.6 | 16.2 | 4.2 | 14.1 | 4.7 |

Surprisingly, the present inventors have found that the administration per os of palmitoylethanolamide in the ultra-micronized form determinates a quick and huge increase of 2-AG in blood (which increase is higher than 400% compared to the basal levels). Such increase results to be vastly higher compared to that obtained, under identical conditions, with the administration of micronized palmitoylethanolamide (increase of about 70%). Without being bond to any theory, the observation that the passage kinetics of palmitoylethanolamide in the blood, following administration, results to be substantially identical between the micronized form and the ultra-micronized one may induce to think that the huge increase of 2-AG, following the administration of the ultra-micronized palmitoylethanolamide, depends on the increased synthesis of 2-AG at the level of the nervous structures protected by blood-brain barrier and/or blood-spinal cord barrier, induced by the administered product. In fact, it is known that the biosynthesis of 2-AG occurs—on demand—mainly at the level of central nervous structures such as spinal cord and brain.

The inventors have hypothesized that such increase can be responsible or co-responsible for the pharmacological effects then observed at the level of the spinal cord, after administration of ultra-micronized palmitoylethanolamide, as it will be detailed in the following of the present description.

Pharmacological Activity

Chronic Inflammation of the Peripheral Nerve with Occurrence of Neuropathic Pain After sciatic nerve ligation—CCI (carried out as described by Costa et al., Pain 2008; 139:541-550), a series of altered spinal parameters have been assessed in the mouse, following peripheral damage, and related to the activation of microglial cells induced by the peripheral chronic distress. In particular, TNF-alpha, NGF, NF-kB according to the method described by Costa et al. (see supra), and IL-1 alpha according to the method described by Fiorentino et al., 2008; 58(10):3100-3109 have been measured.

Per os treatments have been carried out, by means of tube, using both micronized palmitoylethanolamide suspended in vehicle, and ultra-micronized palmitoylethanolamide suspended in vehicle; the results have been compared to control animals treated with vehicle alone and to animals with sciatic nerve ligation treated with vehicle alone. A 0.5% solution in carboxymethyl cellulose has been used as a vehicle.

The administration of the vehicle and the two different suspensions containing palmitoylethanolamide has been carried out once per day, starting from the day of the sciatic nerve ligation.

The measurements of the parameters indicated above have been carried out at day 10 from the sciatic nerve ligation, after sacrifice of the test animal and sampling of the spinal area.

The results are reported in table III.

TABLE III

| Groups of animals (10 animals/ group) | Dose measurements at day 10 after ligation (CCI) | | | |
|---|---|---|---|---|
| | TNF-alpha (pg/mg prot) | NGF (pg/mg prot) | NF-kB (pg/mg prot) | IL-1alpha (pg/mg prot) |
| Sham/vehicle (control) | 51.0 ± 2.5 | 28.6 ± 2.0 | 0.49 ± 0.002 | 0.06 ± 0.0002 |
| CCI/vehicle | 66.2 ± 3.1 | 44.0 ± 6.2 | 0.58 ± 0.003 | 32.20 ± 2.5 |
| CCI/micronized PEA | 60.4 ± 3.0 | 38.6 ± 3.0 | 0.53 ± 0.003 | 25.80 ± 2.0 |
| CCI/ultra-micronized PEA | 44.1 ± 2.8 | 10.2 ± 2.0 | 0.44 ± 0.001 | 2.50 ± 0.02 |

The data show that the administration of ultra-micronized PEA, unlike micronized PEA, causes a substantial normalization of all the biochemical parameters under investigation.

Acute Inflammation of Dermo-Epidermal Tissue Due to Immunogenic Stimuli in the Dog Beagle dog spontaneously sensitized to *Ascaris suum* were used. The animals were left under fasting conditions overnight, before the oral administration of palmitoylethanolamide.

The animals were divided into 2 groups of 6 animals each; the first group (group A) was administered, in the form of oral viscous suspension of 0.5% carboxymethyl cellulose, 10 mg/Kg of micronized palmitoylethanolamide; the second group (group B) was administered 10 mg/Kg of ultra-micronized palmitoylethanolamide suspended in the same vehicle.

Before and after the administration of palmitoylethanolamide, a cutaneous reaction was induced by intradermal injection in the lateral toracic region of Asc S1 antigen (100 μg/mL). A 2% solution of Evans Blue in saline was administered endovenously (0.4 mL/Kg) 30 minutes before the intradermal injection of Asc S1 antigen, so as to be able to visualize the dermal reaction area.

The dermal reaction with the Asc S1 antigen was induced in the animals of both groups, before (time 0), at 1, 2, 4, 8, and 24 hours, respectively, after the administration of palmitoylethanolamide. The dermal reaction area was measured 10 minutes after the injection of Asc S1 antigen.

The data are reported in table IV.

TABLE IV

| | Inhibition produced by palmitoylethanolamide on the cutaneous reaction induced by Ascaris suum (%) | |
|---|---|---|
| Time (hours) | Micronized palmitoylethanolamide (10 mg/Kg) Average value | Ultramicronized palmitoylethanolamide (10 mg/Kg) Average value |
| 0 | 0 | 0 |
| 1 | 9.4 ± 2.6 | 20.8 ± 5.4 |
| 2 | 9.3 ± 4.7 | 32.4 ± 4.7 |
| 4 | −2.6 ± 4.2 | 26.0 ± 4.9 |
| 8 | −0.8 ± 2.0 | 15.1 ± 9.6 |
| 24 | −0.2 ± 2.0 | 4.5 ± 6.7 |

The data show that ultra-micronized PEA causes an inhibition of the cutaneous reaction above 20%, in periods of time ranging between 1 and 4 hours after treatment, compared to an almost null inhibition obtained with micronized PEA.

Effect of Palmitoylethanolamide on the Chronic Inflammation of Connective Tissue Due to Occurrence of Carrageenan-Induced Granuloma in the Rat The pharmacological model of granuloma induced, in the rat, by the introduction in the subcutaneous tissue of carrageenan-soaked sponge has been used. The model is described in De Filippis et al., J Cell Mol Med. 2009; 13(6):1086-1095.

Palmitoylethanolamide, in micronized and ultra-micronized form, was administered to two different groups of, animals, by oral route and a solution of 0.5% carboxymethyl cellulose (vehicle) as a vehicle, by means of gastric tube; the third group of animals was administered, with similar modes, the vehicle alone. The administrations were carried out at time 0 (immediately before the introduction of the sponges), and every 12 hours for 3 consecutive days. The unit doses administered were 10 mg/Kg.

The biochemical parameters relative to pro-algogenic mediators were detected, after sacrifice of the animal occurred after 96 hours from the introduction of the sponges, both in the granulomatous tissue (expression of the protein NGF), and at the level of the dorsal root ganglia (RDG) (expression of the protein TNF-alpha and the protein NGF).

The data are reported in table V.

TABLE V

| Groups of animals (10 animals/group) | Dose measurements in the granulomatous tissue Expression of protein NGF (OD = $mm^2$) | Dose measurements in the dorsal root ganglia | |
|---|---|---|---|
| | | Expression of protein NGF (OD = $mm^2$) | Expression of protein TNF-alpha (OD = $mm^2$) |
| Carrageenan + vehicle | 23.3 ± 2.2 | 53.3 ± 3.6 | 196.1 ± 13.2 |
| Carrageenan + micronized PEA | 14.6 ± 2.1 | 50.8 ± 3.0 | 151.1 ± 9.6 |
| Carrageenan + ultra-micronized PEA | 6.1 ± 1.6 | 43.8 ± 3.1 | 96.6 ± 10.4 |

In this case also, ultra-micronized PEA causes a much more marked decrease of NGF levels compared to the micronized PEA.

Effect of Palmitoylethanolamide on the Acute and Chronic Intestinal Inflammation in the Mouse It has been recently shown that abnormalities of the enteric nervous system such as neuronal degeneration and the decrease in the number of the enteric neurons represent critical elements in the pathogenetic mechanism of gastrointestinal disorders such as the Irritable Bowel Syndrome.

An acute inflammation was induced in the animal by means of intra-peritoneal injection of LPS (lipopolysaccharide): the animals were sacrificed after 18 hours from the LPS administration. Instead, a chronic inflammation at the colon level was induced by administering the animal with DNBS (2,4-Dinitrobenzene sulfonic acid): in this case, the animals were sacrificed after 96 hours from the DNBS administration.

In the acute model, palmitoylethanolamide was administered 15 minutes before and 2 hours after the LPS administration. In the chronic model, instead, the palmitoylethanolamide was administered daily for 96 hours after the DNBS administration.

The level of TNF-alpha and the percent variation in the number of mast cells were assessed on intestinal tissue.

The results are reported in table VI.

TABLE VI

| | LPS-induced acute inflammation | | DNBS-induced chronic inflammation | |
|---|---|---|---|---|
| Groups of animals (10 animals/group) | Expression of protein TNF-alpha (OD = $mm^2$) | Percent decrease in the number of tissue mast cells | Expression of protein TNF-alpha (OD = $mm^2$) | Percent decrease in the number of tissue mast cells |
| Vehicle | 142.1 ± 11.2 | 100 | 195.1 ± 14.8 | 100 |
| Micronized PEA | 128.3 ± 10.8 | 86 | 134.8 ± 8.4 | 74 |
| Ultra-micronized PEA | 75.6 ± 12.3 | 41 | 62.9 ± 11.8 | 26 |

Also this model highlights an activity that is much more marked for ultra-micronized PEA than for micronized PEA.

In Vivo Effect of Palmitoylethanolamide on the Beta-Amyloid-Induced Neuroinflammation in Mouse It has been shown how the in vivo administration of beta-amyloid in the mouse induces a reactive gliosis with manifestations corresponding to the ones that are pointed out in the Alzheimer's disease.

C57BL/6 mice with age ranging between 3 and 5 months have been used, divided in 3 different groups (20 animals per group). Two groups were administered, per os by means of a tube, with micronized and ultra-micronized palmitoylethanolamide, respectively, with a 0.5% solution of carboxymethyl cellulose as a vechicle. The administrations were carried out daily for 8 days successive to the inoculation of the beta-amyloid. The third group was administered with the vehicle alone. After sacrifice of the animal, IL-1 beta and $NO_2$ dose level was measured in the hippocampal homogenate via an immunofluorescence method.

The experimental method described by Esposito et al., Br J Pharmacol. 2007; 151:1272-1279 has been used.

The data are reported in table VII.

TABLE VII

| Groups of animals (10 animals/group) | Hippocampal tissue levels of IL-1 beta (with immunofluorescence method) (count of cells immunopositive to THE-1 beta) | Hippocampal levels of $NO_2$ (in µM/µg of proteins from hippocampal homogeneate) |
|---|---|---|
| Beta amyloid + vehicle | 96.1 ± 7.3 | 9.8 ± 2.3 |
| Beta amyloid + micronized PEA | 86.3 ± 7.9 | 8.2 ± 2.1 |
| Beta amyloid + ultra-micronized PEA | 21.8 ± 5.4 | 3.1 ± 0.6 |

The ultra-micronized PEA highlights, in this case also, a high decrease of the levels of the biological parameters considered, while the micronized PEA shows only a marginal activity.

Clinical Results

Effect of Palmitoylethanolamide on the Control of the Peripheral Neuropathic Pain in Subjects Affected by Multiple Sclerosis In order to assess the effect of Palmitoylethanolamide on the control of the neuropathic pain in Multiple Sclerosis, micronized and ultra-micronized palmitoylethanolamide, respectively, in the form of tablets having identical composition in excipients, was administered to two groups of patients, suitably randomized (10 patients for group), all being affected by Multiple Sclerosis, having neuropathic pain at the lower limbs (Central Pain Dyndrome), characterized by dysesthesia, allodynia, paresthesias, cramp-likepains, and foot burning feeling; the dosing used was 600 mg per day for 60 days. The pain intensity was measured with a VAS (Visual Analogue Scale) scale both before and at the end of the treatment with palmitoylethanolamide.

A marked decrease of the pain is evidenced in patients treated with ultra-micronized PEA. A statistical analysis has been carried out with the Wilcoxon test for paired data; the obtained results show a high statistical significance ($p=0.001$).

The data are reported in table VIII.

TABLE VIII

| Groups of patients (10 patients/group) | VAS before the treatment (average value) | VAS after the treatment of 60 days (average value) |
|---|---|---|
| Micronized palmitoylethanolamide | 6.52 | 4.22 |
| Ultra-micronized palmitoylethanolamide | 6.52 | 2.85 |

Therefore, it is an object of the present invention a pharmaceutical formulation for human or veterinary use, containing ultra-micronized palmitoylethanolamide, as defined above, together with a pharmaceutically acceptable excipient.

In an embodiment, more than 99% by weight, or about 99.9% by weight, of palmitoylethanolamide has particle sizes lower than 6 microns.

In an embodiment, between 55% and 65% by weight, or between 59% and 60% by weight, of palmitoylethanolamide has particle sizes lower than 2 microns.

In an embodiment, between 13% and 17% by weight, or between 14% and 15% by weight, of palmitoylethanolamide has particle sizes lower than 1 micron.

In an embodiment, between 1% and 3% by weight, or about 2% by weight, of palmitoylethanolamide has particle sizes lower than 0.6 microns.

The formulation according to the present invention can be suitable for a oral, buccal, parenteral, rectal, or transdermal administration, or it can exist in a form that is suitable for the administration by inhalation or insufflation (both per os and via the nasal route).

For the oral administration, the pharmaceutical compositions can be, for example, in the form of tablets or capsules that are prepared in the conventional manner, with pharmaceutically acceptable excipients such as binding agents (for example, pregelatinized corn starch, polyvinylpyrrolidone, or hydroxypropyl methyl cellulose); filling agents (for example, lactose, microcrystalline cellulose, or calcium hydrogen phosphate); lubricants (for example, magnesium stearate, talc, or silica); disgregating agents (for example, potato starch, or sodium starch glycolate); or imbibing agents (for example, sodium lauryl sulphate). The tablets may be coated with the methods well known in the art. The liquid preparations for oral administration can be, for example, in the forms of solutions, syrups, or suspensions, or they can be in the form of freeze-dried products to be reconstituted, before use, with water or other suitable vehicles. Such liquid preparations can be prepared through the conventional methods with the pharmaceutically acceptable additives, such as suspending agents (for example, sorbitol syrup, cellulose derivatives, or edible hydrogenated fats); emulsionating agents (for example, lecithin or acacia); non-aqueous vehicles (for example, almond oil, oily esters, ethyl alcohol or fractionated vegetal oils); and preservatives (for example, methyl- or propyl-p-hydroxybenzoates or sorbic acid). The preparation can also suitably contain aromas, colorants and sweetening agents.

The preparations for oral administration can be formulated in a suitable way to allow the controlled release of the active principle.

For the buccal administration, the compositions can be in the form of tablets that are formulated in the conventional manner, suitable for an absorption at the level of the buccal mucose. Typical buccal formulations are the tablets for sublingual administration.

The formulations of the present invention can be adapted for a parenteral administration by injection. The formulations for the injections can be presented in the form of a single dose, for example, in ampoules, with the addition of a preservative. The compositions can be in such a form as suspensions, solutions, or emulsions in oily or aqueous vehicles, and may contain prescribed agents, such as suspending agents, stabilizers, and/or dispersants. Alternatively, the active principle can be in the form of powder to be reconstituted, before the use, with a suitable vehicle, for example, with sterile water.

According to the present invention, the compound can also be formulated according to rectal compositions, such as suppositories or retention enema, for example, containing the base components of the typical suppositories, such as cocoa butter or other glycerides.

In addition to the compositions described before, the PEA can also be formulated as a depot preparation. Such long-acting formulations can be administered via implant (for example, subcutaneously, transcutaneously, or intramuscularly), or by intramuscular injection. Therefore, for example, it can contain appropriate polymeric or hydrophobic materials (for example, in the form of an emulsion in a suitable oil) or ionic exchange resins, or as minimally soluble derivatives, for example, as a minimally soluble salt.

According to the present invention, the dose of palmitoylethanolamide proposed for the administration to a man (having a body weight of about 70 Kg) ranges from 0.1 mg to 2 g, and preferably from 50 mg to 1000 mg of the active principle per dose unit. The dose unit can be administered, for example, from 1 to 4 times per day. The dose will depend on the route of administration selected. It shall be considered that it could be necessary to make continuous variations of the dosing according to the patient's age and weight, and also to the severity of the clinical condition to be treated. The exact dose and route of administration will be ultimately at the discretion of the attending physician or veterinary.

In an embodiment, the ultra-micronized PEA is used in combination with anti-oxidant substances, preferably selected from the group consisting in Quercetin, Resveratrol, Polydatin, Luteolin, Tocopherol, and Thioctic Acid in a therapeutically effective amount.

Examples of formulations containing ultra-micronized PEA (PEA UM) according to the invention are reported herein below.

FORMULATION EXAMPLES

Example 1

Each tablet contains:

| UM PEA | mg 300.00 |
|---|---|
| Microcrystalline cellulose | mg 78.47 |
| Sodium crosscaramellose | mg 45.00 |

-continued

| | |
|---|---|
| Polyvinylpyrrolidone | mg 10.00 |
| Magnesium stearate | mg 4.00 |
| Polysorbate 80 | mg 2.00 |

Example 2

Each tablet contains:

| | |
|---|---|
| UM PEA | mg 600.00 |
| Microcrystalline cellulose | mg 156.94 |
| Sodium crosscaramellose | mg 90.00 |
| Polyvinylpyrrolidone | mg 20.00 |
| Magnesium stearate | mg 8.00 |
| Polysorbate 80 | mg 4.00 |

Example 3

Each bilayer tablet contains:

| | |
|---|---|
| Layer a | |
| UM PEA | mg 400.00 |
| Pharmacologically acceptable excipients | mg 200.00 |
| Layer b | |
| Trans-Polydatin | mg 40.00 |
| Pharmacologically acceptable excipients | mg 25.00 |

Example 4

Each bilayer tablet contains:

| | |
|---|---|
| Layer a | |
| UM PEA | mg 600.00 |
| Pharmacologically acceptable excipients | mg 280.00 |
| Layer b | |
| Luteolin | mg 80.00 |
| Pharmacologically acceptable excipients | mg 46.00 |

Example 5

Each three-layer tablet contains:

| | |
|---|---|
| Layer a | |
| Hyaluronic acid, sodium salt | mg 20.00 |
| Pharmacologically acceptable excipients | mg 15.00 |
| Layer b | |
| UM PEA | mg 300.00 |
| Pharmacologically acceptable excipients | mg 152.00 |
| Layer c | |
| Hyaluronic acid, sodium salt | mg 20.00 |
| Pharmacologically acceptable excipients | mg 15.00 |

Example 6

A 5 g dose of orally disintegrating microgranules, for pediatric use, contains:

| | |
|---|---|
| UM PEA | mg 50.00 |
| Non-cariogenic sugar | mg 200.00 |
| Pharmacologically acceptable excipients q.s. to | g 5.00 |

Example 7

A 5 mL dose of sterile suspension, for pediatric use, contains:

| | |
|---|---|
| UM PEA | mg 80.00 |
| Carboxymethyl cellulose | mg 25.00 |
| Bidistilled water q.s. to | mL 5.00 |

Example 8

A 5 g dose of orally disintegrating microgranules contains:

| | |
|---|---|
| UM PEA | mg 600.00 |
| Luteolin | mg 100.00 |
| Non-cariogenic sugar | mg 200.00 |
| Pharmacologically acceptable excipients q.s. to | g 5.00 |

Example 9

Each 5 mL sterile monodose bilayer container contains:

| | |
|---|---|
| In the aqueous gel: | |
| Hyaluronic acid, sodium salt | mg 80.00 |
| Bidistilled water, q.b. to | mL 2.50 |
| In the oily gel: | |
| UM PEA | mg 600.00 |
| Glyceryl monostearate (Geleol) | mg 40.00 |
| Vegetal oil q.s. to | mL 2.50 |

Example 10

Each 100 mL sterile bottle for intraperitoneal application contains:

| | |
|---|---|
| UM PEA | g 2.00 |
| Hyaluronic acid, sodium salt | g 2.00 |
| Bidistilled water q.s. to | mL 100.00 |

Example 11

Each soft gelatin capsule, for veterinary use (dog and cat), contains:

| | |
|---|---|
| UM PEA | mg 100.00 |
| Phosphatidylserine | mg 50.00 |

-continued

| | |
|---|---|
| Resveratrol | mg 60.00 |
| Pharmaceutically acceptable oily excipients | mg 300.00 |

The above-described formulations can be prepared according to methods that are well known to those skilled in the art, such as those described in Remington's Pharmaceutical Sciences Handbook, Mack Pub. Co., N.Y., USA, 17th edition, 1985.

The PEA is a commercial compound, or it can be anyway prepared according to methods that are well known to those skilled in the art.

The formulations of the present invention can be used for the treatment or prophylaxis of neuroimmunogenic inflammatory diseases at the level of peripheral organs and/or neuroinflammatory diseases, also associated to neurodegeneration at the level of the spinal cord and/or brain.

In particular, the present invention relates to the above-described formulations for the treatment of:

1—neuroimmunogenic inflammatory processes at the level of peripheral organs and apparatuses of the body, supporting diseases such as a) the Irritable Bowel Syndrome; b) the interstitial cistitis and the recurrent cistites; c) the vulvodynias and the vestibulodynias; d) the vulvar vestibulitis; e) the endometrial lesions; f) the miastenia gravis g) the chronic abacterial prostatitis of type IIIA and IIIB; h) the arthropathies of traumatic or degenerative or immunologic origin affecting the mobile and/or semi-mobile joints; i) the painful diseases of the intervertebral discs due to neo-innervation and neo-vascolarization of the cartilaginous tissue and the annexed ligamentous structures—pulpy nucleus (nucleus pulposus) and/or fibrous rings (anulus fibrosus), anterior and posterior longitudinal ligaments, supraspinous ligament—; l) the cephalalgic syndromes due to inflammation of the meningeal tissue; m) the inflammations of the mucous and mucocutaneous tissues of the oral cavity and the dental pulp; n) the recurrent fevers on auto-inflammatory basis of PFAPA type in the pediatric age; o) the dermo-epidermal neuralgias of the small fibres, nociceptive and/or pruriceptive, with a neuropathic basis as the postherpetic neuralgia, the diabetes-associated neuralgias, the neuralgia due to HIV infection, the neuropathic and/or psicogenic itches; p) the granulomas affecting the dermo-epidermal tissue; q) the adherential syndromes due to peritonitis and/or laparotomic and/or laparoscopic surgical events; r) the dermatologic diseases, also with immunological genesis, characterized by neuroinflammatory processes, both acute and chronic;

2—Neuroinflammatory processes, also associated to neurodegeneration, that occur and affect nervous structures of the spinal cord following: a) traumatic, dismetabolic, or degenerative noxae such as the medullary canal stenoses, such as the spondylosis and the spondylolisthesis or the traumatic lesions from flexo-extension of the spine; b) inflammatory distresses affecting encephalic nervous structures (stroke, multiple sclerosis, Parkinson's disease, fibromyalgic syndrome) with consequent occurrence of peripheral pains, currently classified as "Central Pain Syndromes"; c) chronic inflammatory distresses of the Osteoarticular System and the Peripheral Nervous System, mainly characterized by chronic and/or neuropathic pain;

3—neuroinflammatory processes, also associated to neurodegeneration, that occur and affect nervous structures of given encephalic areas following traumatic, neuro-toxic, dismetabolic, or degenerative noxae, such as the hypoxic distress states (stroke, TIA-Trans Ischemic Attack), the senile and presenile dementias also of the Alzheimer type, cranioencephalic traumas, Parkinson's disease, Multiple Sclerosis, Amiotrophic Lateral Sclerosis.

As described before, without being bond to a particular theory, it seems that such pharmacological effect is mediated by the ability of ultra-micronized PEA to significantly increase the release of the endocannabinoid 2-arachidonoylglycerol (2-AG).

Therefore, it is a further object of the invention a formulation containing ultra-micronized PEA as defined above, for the treatment or prophylaxis of neuroimmunogenic inflammatory diseases at the level of peripheral organs, and/or neuroinflammatory diseases, also associated to neurodegeneration at the level of the spinal cord and/or brain, so as to obtain in the serum of the treated subject, in a period of time between 1 and 3 hours after said treatment, concentrations of 2-arachidonoylglycerol that are higher, preferably from 3 to 5 fold higher, than the concentrations before the treatment.

It shall be apparent that, to the present invention, one of ordinary skill in the art, with the aim of meeting contingent and specific needs, will be able to make further modifications and variations, all of which are within the protection scope of the invention, as defined by the following claims.

The invention claimed is:

1. A method of treatment or prophylaxis of neuroimmunogenic inflammatory diseases at the level of peripheral organs, and/or neuroinflammatory diseases, also associated to neurodegeneration at the level of the spinal cord and/or brain, the method comprising administering to a patient in need thereof a therapeutically effective amount of palmitoylethanolamide in the ultra-micronized form, wherein said palmitoylethanolamide has an MDSC spectrum with exothermal transition at temperatures ranging between 101° C. and 103° C., and a spectrum XRD as reported in the following table:

| Peak [2-Theta (°)] |
|---|
| 6.155 |
| 8.194 |
| 12.271 |
| 18.438 |
| 20.844 |
| 21.780 |
| 22.532 |
| 24.003 |
| 25.256 |
| 31.289 |
| 36.770 |
| 38.759. |

2. The method according to claim 1, wherein the palmitoylethanolamide is administered together with pharmaceutically acceptable excipients.

3. The method according to claim 1, wherein more than 99% by weight, or about 99.9% by weight, of palmitoylethanolamide has particle sizes lower than 6 microns.

4. The method according to claim 1, wherein between 55% and 65% by weight, or between 59% and 60% by weight, of palmitoylethanolamide has particle sizes lower than 2 microns.

5. The method according to claim 1, wherein between 13% and 17% by weight, or between 14% and 15% by weight, of palmitoylethanolamide has particle sizes lower than 1 microns.

6. The method according to claim 1, wherein between 1% and 3% by weight, or about 2% by weight, of palmitoylethanolamide has particle sizes lower than 0.6 microns.

7. The method according to claim 1, wherein said palmitoylethanolamide is administered in combination with an antioxidant compound.

8. The method according to claim 7, wherein said antioxidant compound is selected from Quercetin, Resveratrol, Polydatin, Luteolin, Tocopherol, and Thioctic Acid.

9. The method according to claim 1, wherein said diseases comprise:

neuroimmunogenic inflammatory processes at the level of peripheral organs and apparatuses of the body, supporting diseases such as a) the Irritable Bowel Syndrome; b) the interstitial cistitis and the recurrent cistites; c) the vulvodynias and the vestibulodynias; d) the vulvar vestibulitis; e) the endometrial lesions; f) the miastenia gravis g) the chronic abacterial prostatitis of type IIIA and IIIB; h) the arthropathies of traumatic or degenerative or immunologic origin, affecting the mobile and/or semi-mobile joints; i) the painful diseases of the intervertebral discs due to neo-innervation and neo-vascolarization of the cartilaginous tissue and the annexed ligamentous structures—pulpy nucleus, i.e. nucleus pulposus, and/or fibrous rings, i.e. anulus fibrosus, anterior and posterior longitudinal ligaments, supraspinous ligament; l) the cephalalgic syndromes due to inflammation, of the meningeal tissue; m) the inflammations of the mucous and mucocutaneous tissues of the oral cavity and the dental pulp; n) the recurrent fevers with autoinflammatory basis of PFAPA type in the pediatric age; o) the dermo-epidermal neuralgias of the small fibres, nociceptive and/or pruriceptive, with neuropathic basis as the postherpetic neuralgia, the diabetes-associated neuralgias, the neuralgia due to HIV infection, the neuropathic and/or psicogenic itches; p) the granulomas affecting the dermo-epidermal tissue; q) the adherential syndromes due to peritonitis and/or laparotomic and/or laparoscopic surgical events; r) the dermatologic diseases, also with immunological genesis, characterized by neuroinflammatory processes, both acute and chronic;

neuroinflammatory processes, also associated to neurodegeneration, which occur and affect the nervous structures of the spinal cord following: a) traumatic, dismetabolic, or degenerative noxae such as the medullary canal stenoses, such as the spondylosis and the spondylolisthesis or the traumatic lesions from flexo-extension of the spine; b) inflammatory distresses affecting encephalic nervous structures including, stroke, multiple sclerosis, Parkinson's disease, fibromyalgic syndrome with consequent occurrence of peripheral pains, currently classified as "Central Pain Syndromes"; c) chronic inflammatory distresses of the Osteoarticular System and the Peripheral Nervous System, mainly characterized by chronic and/or neuropathic pain;

neuroinflammatory processes, also associated to neurodegeneration, which occur and affect nervous structures of given encephalic areas following traumatic, neurotoxic, dismetabolic, or degenerative noxae, such as the hypoxic distress states including, stroke, TIA-Trans Ischemic Attack, the senile and presenile dementias also of the Alzheimer type, cranio-encephalic traumas, Parkinson's disease, Multiple sclerosis, Amiotrophic Lateral Sclerosis.

10. The method according to claim 1, wherein said treatment is carried out so as to obtain, in the serum of the treated subject, in a period of time between 1 and 3 hours after said treatment, concentrations of 2-arachidonoylglycerol from 3 to 5 fold higher than the concentrations before the treatment.

* * * * *